United States Patent [19]

Grollier et al.

[11] Patent Number: 5,059,606

[45] Date of Patent: Oct. 22, 1991

[54] COMBINATION OF PYRIMIDINE DERIVATIVES AND CALCIUM ANTAGONISTS TO INDUCE AND STIMULATE HAIR GROWTH AND REDUCE HAIR LOSS

[75] Inventors: Jean F. Grollier, Paris; Georges Rosenbaum, Asnières, both of France

[73] Assignee: L'Oreal, Paris, France

[21] Appl. No.: 281,273

[22] Filed: Dec. 8, 1988

[30] Foreign Application Priority Data

Dec. 9, 1987 [LU] Luxembourg .......................... 87068

[51] Int. Cl.$^5$ ............................................ A61K 31/505
[52] U.S. Cl. ................................. 514/231.5; 514/269; 514/275
[58] Field of Search ...................... 514/275, 231.5, 269

[56] References Cited

U.S. PATENT DOCUMENTS 4,139,619  2/1979  Chidsey ................................. 424/45
4,820,512  4/1989  Grollier ................................. 424/70

FOREIGN PATENT DOCUMENTS 905375  12/1986  Belgium .

Primary Examiner—Nicholas S. Rizzo
Attorney, Agent, or Firm—Fleit, Jacobson, Cohn, Price, Holman & Stern

[57] ABSTRACT

A combination intended to induce and stimulate hair growth and reduce hair loss comprising a first component containing at least one calcium antagonist in a physiologically acceptable medium and a second component containing, in a physiologically acceptable medium, at least one pyrimidine derivative having the formula:

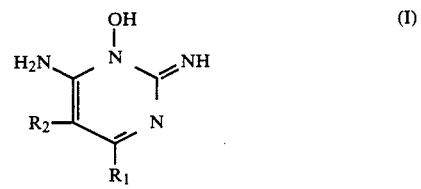

In formula (I) $R_1$ represents the group

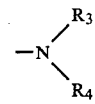

in which $R_3$ and $R_4$ are independent of each other and represent hydrogen, an alkyl, alkenyl, alkylaryl or cycloalkyl group, or $R_3$ and $R_4$ form a heterocycle with the nitrogen atom joined thereto, and represent an aziridinyl, azetidinyl, pyrrolidinyl, piperidinyl, hexahydroazepinyl, heptamethyleneimine, octamethyleneimine, morpholine or 4-alkylpiperazidinyl group, the heterocyclic groups further being substitutable at the carbon atoms by one to three low alkyl, hydroxy or alkoxy groups. In formula (I) $R_2$ represents a hydrogen atom, an alkyl, alkenyl, alkylalkoxy, cycloalkyl, aryl, alkylaryl, arylalkyl, alkylarylalkyl, alkoxyarylalkyl or haloarylalkyl group. The addition salts of physiologically acceptable acids may also be employed. The first and second components may form part of the same composition or may be used separately, either simultaneously or in successive or separate stages.

21 Claims, No Drawings

COMBINATION OF PYRIMIDINE DERIVATIVES AND CALCIUM ANTAGONISTS TO INDUCE AND STIMULATE HAIR GROWTH AND REDUCE HAIR LOSS

BACKGROUND OF THE INVENTION

Field of the Invention

The invention concerns a novel combination of a calcium antagonist and a pyrimidine derivative intended to induce and stimulate hair growth, also a method of treatment using said combination.

An individual has about 100 000 to 150 000 hairs on his head and normally 50 to 100 are lost daily. The number is maintained primarily because a hair has a pilary life cycle comprising formation, growth and fall before being replaced by a new hair appearing from the same follicle.

There are three phases in the pilary cycle: the anagenous, catagenous and telogenous phases.

During the first, anagenous, phase the hair goes through a period of active growth associated with intense metabolic activity in the root.

The second, catagenous, phase is transient and characterized by slowing of mitotic activities. During this phase the hair undergoes involution, the follicle atrophies and its dermal implantation appears increasingly raised.

The final, telogenous, phase corresponds to the follicle's rest period and the hair finally falls out, pushed out by a newly-formed anagenous hair.

This continuous physical renewal process evolves naturally during ageing with the hair becoming finer and the cycles shorter.

Alopecia occurs when this physical renewal process is accelerated or perturbed, ie the growth phases are shortened, the hair goes into the telogenous phase earlier and more hair falls out. Successive growth cycles result in finer and finer, shorter and shorter hair, gradually ending up as unpigmented down. This phenomenon may result in baldness.

"Minoxidil" (6-amino-1,2,-dihydro,1-hydroxy-2-imino-4-piperidinopyrimidine) has already been used in treating hair loss in topical compositions which reduce or end the effects of alopecia, induce and stimulate hair growth and reduce hair loss.

Orally or parenterally administered calcium antagonists are known in the therapy and treatment of cardio-vascular ailments.

It has now, surprisingly been discovered that combining calcium antagonists (which in themselves neither induce or stimulate hair growth nor slow hair loss) with certain pyrimidine derivatives produces the surprising effect of improving the induction and stimulation of hair growth and ameliorating the slowing of hair loss.

In particular, the combination begins to act more quickly than these compositions in isolation. Because of the combination, a lower concentration of the pyrimidine derivative can be employed.

The efficacity or speed of action of a composition for the treatment of alopecia can be especially well determined using a trichogram and in particular a phototrichogram which, inter alia, allows the percentage of hair in the anagenous phase to be determined with respect to the hair in the telogenous phase.

In particular, a combination according to the invention will increase this percentage compared with that when the compositions are used separately.

One object of the invention is to provide a combination of a calcium antagonist and a pyrimidine derivative intended to induce or stimulate hair growth and reduce hair loss.

Another object of the invention is to provide a cosmetic and/or pharmaceutical composition comprising this combination.

A further object of the invention is to provide a device having several compartments containing said combination.

Further objects of the invention will become apparent from the following description and examples.

SUMMARY OF THE INVENTION

A combination according to the invention intended to induce and stimulate hair growth and reduce hair loss is primarily characterized in that it comprises:

a) a first component comprising at least one calcium antagonist in a physiologically acceptable medium; and b) a second component containing, in a physiologically acceptable medium, a pyrimidine derivative having formula:

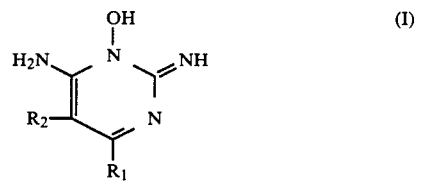

wherein $R_1$ represents the group

in which $R_3$ and $R_4$ are independent of each other and represent hydrogen, an alkyl, alkenyl, alkylaryl or cycloalkyl group, or $R_3$ and $R_4$ form a heterocycle with the nitrogen atom joined thereto, and represent an aziridinyl, azetidinyl, pyrrolidinyl, piperidinyl, hexahydroazepinyl, heptamethyleneimine, octamethyleneimine, morpholine or 4-alkyl-piperazidinyl group, the heterocyclic groups further being substitutable at the carbon atoms by one to three low alkyl, hydroxy or alkoxy groups; and $R_2$ represents a hydrogen atom, an alkyl, alkenyl, alkylalkoxy, cycloalkyl, aryl, alkylaryl, arylalkyl, alkylarylalkyl, alkoxyarylalkyl or haloarylalkyl group, as well as the addition salts of physiologically acceptable acids; in which combination said first and second components form part of the same composition or are intended for separate use, either simultaneously or in successive or separate stages.

More particularly, said calcium antagonist is selected from the group comprising papaverine derivatives, 1,4-dihydropyridine derivatives, benzothiazepine derivatives, cinnamypiperazine derivatives, nicergoline and bepridil.

Particularly preferred papaverine derivatives are: bis1,7-(3,4-dimethoxyphenyl)-5-methyl-1-isopropyl1-cyano-5-azaheptane (verapamil) and its hydrochloride and 5[-methylamino-[2-(3,5-dimethoxyphenyl)ethyl]]-2-isopropyl-2-(3,4,5-trimethoxyphenyl) valeronitrile (gallopamil).

1,4-dihydropyridine derivatives are selected from the group comprising: 4-(2'-nitrophenyl)-2,6-dimethyl-3,5-dicarbomethoxy-1,4-dihydropyridine (nifedipine); 4-(3'-nitrophenyl)-2,6-dimethyl-3-carbomethoxy-5-(methylbenzylamino)-carboxyethoxy-1,4-dihydropyridine )nicardipine) and its hydrochloride; 4-(3'-nitrophenyl-2,6-dimethyl-3-carbo-2-methoxyethoxy)-5-carboisopropoxy-1,4-dihydropyridine (nimodipine); 4-(3'-nitrophenyl)-2,6-dimethyl-3,5-dicarbo-2-propoxyethoxy-1,4-dihydropyridine (niludipine); 4-(2'3'-dichlorophenyl)-2,6-dimethyl-3-carboethoxy-5-carbomethoxy-1,4-dihydropyridine (felodipine); 4-(3'-nitrophenyl)-2,6-dimethyl-3-carboethoxy-5-carbomethoxy 1,4-dihydropyridine (nitrendipine); 4-(3'nitrophenyl)-2-cyano-6-methyl-3-carbomethoxy-5-carbo-(1-methylethoxy)-1,4-dihydropyridine (nilvadipine); 4-(4'-benzofurazanyl)-2,6-dimethyl-3-carbomethoxy-5-carbo-(1-methylethoxy)-1,4dihydropyridine (isradipine)-4-(2'-nitrophenyl)-2,6-dimethyl-3-carboisobutoxy-5-carbomethoxy-1,4dihydropyridine (nisoldipine).

Particularly preferred benzothiazepine derivatives are 3-acetyloxy-5-[2-(dimethylamino)ethyl]-2,3-dihydro-2-(4-methoxyphenyl)-1,5-benzothiazepine-4 (5H)-one (diltiazem) and its hydrochloride.

Particularly preferred cinnamylpiperazines are 1-cinnamyl-4-diphenylmethylpiperazine (cinnarizine), its hydrochloride and its clofibrate and 1-cinnamyl-4-di[(parafluorophenyl)methyl] piperazine (flunarizine) and its hydrochloride.

A particularly preferred nicergoline is (10-methoxy-1,6-dimethylergoline)-8- methanol 5-bromonicotinate.

A particularly preferred bepridil is 1-isobutoxy 2-pyrrolidino-3-N-benzylanilinopropane.

Most particularly preferred calcium antagonists are: verapamil, nifedipine, nicardipine, diltiazem, cinnarizine and flunarizine.

In substances having formula (I), "alkyl or alkoxy" group preferably defines a group containing one to four carbon atoms; "alkenyl" group preferably defines a group containing two to five carbon atoms; "aryl" group preferably defines a phenyl group and "cycloalkyl" group preferably defines a group containing four to six carbon atoms.

Particularly preferred substances having formula (I) are those where R2 represents hydrogen and R1 represents the group:

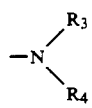

where R3 and R4 represent a piperidinyl cycle, also their salts such as the sulfate, for example.

A particularly preferred substance of this type is 6-amino-1,2-dihydro-1-hydroxy-2-imino-4-piperidinopyrimidine, known under the trade name "Minoxidil".

The calcium antagonist is preferably present in the first component in a proportion of between 0.01 and 10% by weight, preferably between 0.01 and 5% by weight and particularly between 0.1 and 3% by weight. The pyrimidine derivative having formula (I) is preferably present in the second component in a proportion of between 0.05 and 10% by weight, preferably between 0.05 and 5% by weight, and particularly between 0.5 and 4% by weight.

When the first and second components are used in a single composition, the calcium antagonist is preferably present in a proportion of between 0.01 and 5% by weight and preferably between 0.05 and 3% by weight with respect to the total composition weight; the pyrimidine derivative having formula (I) is employed in a proportion of between 0.05 and 6% by weight, preferably between 0.1 and 5% and particularly between 0.5 and 2% by weight with respect to the total composition weight.

Physiologically acceptable media which could be employed include water, water/solvent mixtures or mixtures of cosmetically or pharmaceutically acceptable organic solvents.

More particularly, solvents such as the following may be used: $C_1$ to $C_4$ low alcohols, for example ethanol, isopropanol, tert-butanol; alkyleneglycols such as propyleneglycol; and alkylethers of mono- and dialkyleneglycol, most particularly the monoethylether of ethyleneglycol, the monomethylether of propyleneglycol and the monoethylether of diethyleneglycol.

When used in an aqueous medium, these solvents are preferably present in proportions of between 1 and 80% by weight with respect to the total composition weight.

The physiologically acceptable media may be thickened if desired. Thickening or gelling agents which are known in the art may be used, particularly heterobiopolysaccharides such as xanthane gum or scleroglucanes, cellulose derivatives and reticulated or unreticulated acrylic polymers.

Thickeners are preferably present in proportions of between 0.1 and 5% by weight, particularly between 0.4 and 3% by weight with respect to the total weight of each component when they are used separately or with respect to the total weight of a composition containing both the first and second components.

Compositions constituted either by the first and second components separately or both components together may contain any other additives which are in general use in topical cosmetic or pharmaceutical compositions. In particular, preservatives, complexing agents, dyes, alkalizing or acidifying agents, surfactants, anionic, cationic, nonionic and amphoteric agents or mixtures thereof, and anionic, cationic, nonionic and amphoteric polymers or mixtures thereof may be employed.

Composition pH may vary between 4 and 9.

These compositions may also be packaged under pressure in an aerosol device.

In the second component, pyrimidine derivatives having formula (I) may be present either dissolved in the physiologically acceptable medium, or entirely or partially in suspension in this medium, particularly as particles having a granulometry below 80 microns, preferably below 20 microns and particularly below 5 microns.

A first embodiment of the invention consists in using the combination defined above in a single composition containing the first and second components.

A particularly preferred embodiment of the invention consists in storing the first and second components in separate means and preparing the composition containing the calcium antagonist and the pyrimidine derivative having formula (I) extemporaneously immediately prior to application.

Finally, a further embodiment consists in applying the first and second components separately, either simultaneously or in successive or separate stages.

A combination according to the invention may in this case be packaged as a kit in a device having several compartments whose first compartment contains the first component comprising the calcium antagonist and whose second compartment contains the second component comprising the pyrimidine derivative having formula (I). This device may further comprise mixing means for preparing the composition just prior to application.

A treatment to induce and stimulate hair growth and reduce hair loss consists principally in applying the combination defined above to the areas of the scalp affected by alopecia, either using a single composition or by applying the first and then the second component or vice-versa successively or in separate stages.

A preferred method of application consists in applying 1 to 5 g of single composition or of each of the first and second components to the area affected by alopecia, once or twice a day, one to seven days a week for a period of one to six months.

The treatment method has the characteristics of a therapeutic treatment in that the inventive combination has a therapeutic action on the biological mechanisms of the pilary cycle and its dysfunction.

An object of the invention is thus constituted by the use of a combination which induces or stimulates hair growth and reduces hair loss.

The inventive method also has the characteristics of a cosmetic treatment method in that it improves the hair or scalp.

EXAMPLES OF THE INVENTION

The following examples are intended to illustrate the invention without in any way limiting its scope.

EXAMPLE 1

A lotion having the following composition was prepared:

| | |
|---|---|
| verapamil hydrochloride | 0.60 g |
| Minoxidil | 1.00 g |
| propyleneglycol | 20.00 g |
| ethanol | 50.00 g |
| water | qsp 100.00 g |

EXAMPLE 2

A lotion having the following composition was prepared:

| | |
|---|---|
| diltiazem hydrochloride | 0.90 g |
| Minoxidil | 1.00 g |
| ethanol | 95.00 g |
| propyleneglycol | qsp 100.00 g |

EXAMPLE 3

A lotion having the following composition was prepared:

| | |
|---|---|
| nifedipine | 0.15 g |
| Minoxidil | 1.00 g |
| propyleneglycol | 20.00 g |
| ethanol | 50.00 g |
| water | qsp 100.00 g |

EXAMPLE 4

The following first and second compositions (A) and (B) were packaged in kit form:

| | |
|---|---|
| Composition (A): | |
| flunarizine hydrochloride | 0.20 g |
| ethanol | 95.00 g |
| propyleneglycol | qsp 100.00 g |
| Composition (B): | |
| Minoxidil | 3.00 g |
| propylenegylcol | 20.00 g |
| ethanol | 50.00 g |
| water | qsp 100.00 g |

An extemporaneous mixture of compositions (A) and (B) was applied.

EXAMPLE 5

The following first and second compositions (A) and (B) were packaged in kit form:

| | |
|---|---|
| Composition (A): | |
| nicardipine hydrochloride | 0.60 g |
| propyleneglycol | 20.00 g |
| ethanol | 50.00 g |
| water | qsp 100.00 g |
| Composition (B): | |
| micronised Minoxidil (mean particle size below 2 microns) | 2.00 g |
| reticulated polyacrylic acid M. Wt = 3 million, sold under the trade name "CARBOPOL 934" by GOODRICH | 1.00 g |
| propyleneglycol | 4.50 g |
| 2-amino-2-methyl-1-propanol | qs pH = 7 |
| preservative | qs |
| water | qsp 100.00 g |

The compositions were applied in separate stages: composition (A) in the morning and composition (B) in the evening.

EXAMPLE 6

The following first and second compositions (A) and (B) were packaged in kit form:

| | |
|---|---|
| Composition (A): | |
| cinnarizine | 0.50 g |
| ethanol | 95.00 g |
| propyleneglycol | qsp 100.00 g |
| Composition (B): | |
| Minoxidil | 2.00 g |
| ethanol | 95.00 g |
| propyleneglycol | qsp 100.00 g |

The compositions were applied in separate daily stages: first day, composition (A); second day, composition (B).

In each of examples 1 to 6, following daily application of the composition(s) to areas of the scalp affected by alopecia for three months a considerable improvement in the ratio anagenous/telogenous hair was observed.

EXAMPLE 7

A lotion having the following composition was prepared:

| | |
|---|---|
| diltiazem | 3.00 g |
| Minoxidil | 0.54 g |
| propyleneglycol | 20.00 g |
| ethanol | 50.00 g |
| water | qsp 100.00 g |

EXAMPLE 8

A lotion having the following composition was prepared:

| | |
|---|---|
| cinnarizine | 3.00 g |
| Minoxidil | 0.54 g |
| propyleneglycol | 20.00 g |
| ethanol | 50.00 g |
| water | qsp 100.00 g |

There is claimed:

1. A combination of components, which is useful for the treatment of the hair and scalp and is effective for inducing and stimulating hair growth and for decreasing hair loss, comprising:
  (a) a first component, (A), that contains an effective concentration of at least one calcium antagonist in a physiologically acceptable medium; and
  (b) a second component, (B), that contains, in a physiologically acceptable medium, an effective concentration of at least one compound of formula (I):

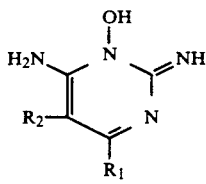

as well as acid addition salts thereof with physiologically acceptable acids,
  wherein:
  $R_1$ is a group having the formula

$R_3$ and $R_4$ are either selected from the group consisting of hydrogen, lower alkyl, alkenyl, alkylaryl and cycloalkyl groups that contain 4 to 6 carbon atoms, in which the alkyl portions are lower alkyl, or $R_3$ and $R_4$, with the nitrogen to which they are each bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinylm, piperidinyl hyxahydroazepinyl, heptamethylenimino, octamethyleneimino, morpholino and 4-(lower alkyl)piperazinyl;
  $R_2$ is selected from the group consisting of hydrogen, lower alkyl, alkenyl, alkoxyalkyl, cycloalkyl groups that contain 4 to 6 carbon atoms, aryl, alkylaryl, arylalkyl, alkylarylalkyl, alkoxyarylalkyl and haloarylalkyl, in which the alkyl portions are lower alkyl radicals;
  said components are intended for use as a composition comprising said components or as separate components that are used either simultaneously, successively or intermittently; and
  each of said concentrations is effective for inducing and stimulating the growth of hair and decreasing its loss when said components are used as said combination.

2. The combination of claim 1, wherein said calcium antagonists are selected from the group consisting of papaverine derivatives, 1,4-dihydropyridine derivatives, benzothiazepine derivatives, cinnamyl-piperazine derivatives, nicergoline and bepridil.

3. The combination of claim 2, wherein said calcium antagonists are selected from the group consisting of verapamil and gallopamil, nifedipine, nicardipine, nimodipine, niludipine, felodipine, nitrenedipine, nisoldipine, nivaldipine, isradipine, diltiazem, cinnarizine and flunarizine.

4. The combination of claim 1, wherein $R_2$ is hydrogen and $R_3$ and $R_4$, with the nitrogen to which they are each bound, form a piperidinyl heterocycle.

5. The combination of claim 4, wherein the compound of formula (I) is 6-amino-1,2-dihydro-1-hydroxy-2-imino-4-piperidinopyrimidine.

6. The combination of claim 1, wherein the concentration of the calcium antagonist in said first component is between 0.01 and 10% by weight, and the concentration of the compound of formula (I) is between 0.05 and 10% by weight.

7. The combination of claim 1, wherein said first and second components are present in a single composition and the concentration of the calcium antagonist in said composition is between 0.01 and 5% by weight and the concentration of the compound of formula (I) in said composition is between 0.5 and 6% by weight.

8. The combination of claim 1, wherein said physiologically acceptable media are water or a mixture of water and one or more organic solvents or a mixture of cosmetically or pharmaceutically acceptable organic solvents.

9. The combination of claim 8, wherein at least one of said first and second components contains a solvent selected from the group consisting of $C_1$ to $C_4$ lower alcohols, alkyleneglycols and alkylethers of monoand dialkyleneglycol.

10. The combination of claim 1, wherein at least one of said first and second components is thickened by including thickening or gelling agents in said medium.

11. The combination of claim 1, wherein at least one of said first and second components also contains a cosmetically or pharmaceutically acceptable additive selected from the group consisting of preservatives, complexing agents, dyes, alkalizing or acidifying agents, anionic surfactants, cationic surfactants, nonionic surfactants, amphoteric surfactants, mixtures of anionic, cationic, nonionic or amphoteric surfactants, anionic polymers, cationic polymers, nonionic polymers, amphoteric polymers and mixtures of anionic, cationic, nonionic or amphoteric polymers.

12. A method for cosmetically treating the hair or scalp, comprising applying an effective amount of the combination of claim 1 to the hair or scalp, wherein said amount is effective for said cosmetic treatment and said components are mixed before use or applied either simultaneously, successively or intermittently to the hair or scalp.

13. A multicompartment device, comprising component (A) in a first compartment and component (B) in a second compartment, wherein:
(a) component (A) contains an effective concentration of at least one calcium antagonist in a physiologically acceptable medium; and
(b) component (B) contains an effective concentration of at least one pyrimidine derivative having a formula:

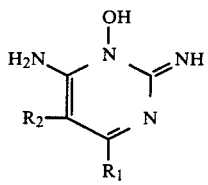

as well as acid addition salts thereof with physiologically acceptable acids;
$R_1$ is a group having the formula

$R_3$ and $R_4$ are either selected from the group consisting of hydrogen, lower alkyl, alkenyl, alkylaryl and cacloalkyl groups that contain 4 to 6 carbon atoms, in which the alkyl portions are lower alkyl, or $R_3$ and $R_4$, with the nitrogen to which they are each bound, form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidinyl, hyxahydroazepinyl, heptamethylenimino, octamethyleneimino, morpholino and 4-(lower alkyl)piperazinyl;
$R_2$ is selected from the group consisting of hydrogen, lower alkyl, alkenyl, alkoxyalkyl, cycloalkyl groups that contain 4 to 6 carbon atoms, aryl, alkylaryl, arylalkyl, alkylarylalkyl, alkoxyarylalkyl and haloarylalkyl, in which the alkyl portions are lower alkyl radicals;
said components are intended for use as a composition comprising said components or as separate components that are used either simultaneously, successively or intermittently; and
each of said concentrations is effective for inducing and stimulating the growth of hair and decreasing its loss when said components are used as said combination.

14. A medicament for the therapeutic treatment of hair loss, comprising the an effective amount of the combination of claim 1 and a carrier suitable for topical application of said medicament to the hair or scalp.

15. A method for preparing the medicament of claim 14, comprising mixing effective amounts of each of the components of said combination with said carrier, wherein said amounts are effective for the therapeutic treatment of hair loss.

16. A combination of components, which is useful for the treatment of the hair and scalp and is effective for inducing and stimulating hair growth and for decreasing hair loss, comprising:

(a) a first component, (A), that contains an effective concentration of at least one benzothiazepine derivative in a physiologically acceptable medium; and
(b) a second component, (B), that contains an effective concentration of at least one compound of formula (I):

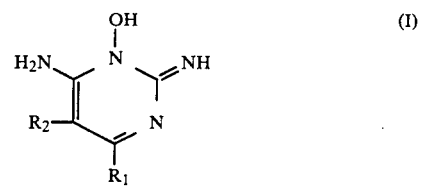

as well as acid addition salts thereof with physiologically acceptable acids,
wherein:
$R_1$ is a group having the formula

$R_3$ and $R_4$ are either selected from the group consisting of hydrogen, lower alkyl, alkenyl, alkylaryl and cycloalkyl groups, or $R_3$ and $R_4$, with the nitrogen to which they are each bound, form a heterocyclic group, which is unsubstituted or is substituted on the carbon atoms with one to three lower alkyl, hydroxy, or alkoxy groups, and which is selected from the group consisting of aziridinyl, azatidinyl, pyrrolidinyl, piperidinyl, hexahydroazapinyl, heptamethylenimino, octamethyleneimino, morpholino and 4-(lower alkyl)piperazinyl;
$R_2$ is selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl,
said components are intended for use as a composition comprising said components or as separate components that are used either simultaneously, successively or intermittently; and
each of said concentrations is effective for inducing and stimulating the growth of hair and decreasing its loss when said components are used as said combination.

17. The combination of claim 16, wherein the benzothiazepine derivative is diltiazem and the compound of formula (I) is 6-amino-1,2-dihydro-1-hydroxy-2-imino-4-piperidinopyrimidine.

18. The combination of claim 6, wherein the concentration of the calcium antagonist in component (A) is between 0.01 and 5% by weight, and the concentration of the compound of formula (I) in component (B) is between 0.05 and 5% by weight.

19. The combination of claim 18, wherein the concentration of said compound of formula (I) is between 0.5 and 4% by weight.

20. The combination of claim 7, wherein the concentration of the calcium antagonist in said composition is between 0.05 and 3% by weight, and the concentration of the compound of formula (I) in said composition is between 0.1 and 5% by weight.

21. The combination of claim 20, wherein the concentration of said compound of formula (I) is between 0.5 and 2% 10 by weight.